United States Patent [19]

Pratt

[11] 4,280,917

[45] Jul. 28, 1981

[54] GREASE COMPOSITIONS AND OXYALUMINUM ACYLATE INTERMEDIATE COMPOSITIONS USEFUL IN THE PREPARATION THEREOF

[75] Inventor: Charles E. Pratt, Signal Mountain, Tenn.

[73] Assignee: Chattem, Inc., Chattanooga, Tenn.

[21] Appl. No.: 96,933

[22] Filed: Nov. 23, 1979

[51] Int. Cl.$^3$ .................. C10M 5/12; C10M 7/16; C10M 1/20
[52] U.S. Cl. .................................. 252/37.7; 252/35; 260/448 R; 260/448 AD
[58] Field of Search ............... 252/35, 37.7; 44/68; 260/448 R, 448 AD

[56] References Cited

U.S. PATENT DOCUMENTS

| | | | |
|---|---|---|---|
| 2,768,138 | 10/1956 | Hotten et al. | 252/35 |
| 3,054,816 | 9/1962 | Rinse | 260/448 |
| 3,345,291 | 10/1967 | Koundakjian et al. | 252/37.7 |
| 3,591,505 | 7/1971 | Polishuk | 252/35 |
| 3,776,846 | 12/1973 | Bailey et al. | 252/32.7 |
| 3,791,972 | 2/1974 | Myers | 252/37.7 |
| 4,132,658 | 1/1979 | Coleman et al. | 252/37.7 |

FOREIGN PATENT DOCUMENTS 825878 12/1959 United Kingdom .

*Primary Examiner*—Patrick Garvin
*Assistant Examiner*—J. V. Howard

[57] ABSTRACT

Mixed aromatic/aliphatic oxyaluminum acylates are provided which have utility for the manufacture of greases without generating by-product alcohol and without requiring the use of water.

26 Claims, No Drawings

GREASE COMPOSITIONS AND OXYALUMINUM ACYLATE INTERMEDIATE COMPOSITIONS USEFUL IN THE PREPARATION THEREOF

BACKGROUND OF THE INVENTION

In the art of making aluminum complex greases, two methods of preparation are commonly employed. In one of these methods, an aluminum alkoxide is dissolved in an oil stock and two mole equivalents of an acid or acid mixture is added thereto. During subsequent heating, reaction occurred releasing one mole of alcohol per mole of acid introduced. Thereafter to the resulting system water is added which reacts with the final remaining alkoxy group thereby releasing the third and final mole of alcohol and producing a hydroxyl group on the aluminum atom. The alcohol produced is removed by distillation and, since the water is typically added in excess, the excess water is likewise removed by distillation. A typical aluminum alkoxide employed in this method is aluminum isopropoxide; see, for example U.S. Pat. No. 3,345,291 issued to Chevron research corporation.

In the second technique, a cyclic aluminum isopropoxide (or other alkoxide) trimer is introduced into a mineral oil. To this mixture is added a carboxylic acid mixture which is approximately equal to two moles of acid per mole of aluminum. When this mixture is heated, reaction occurs which releases one mole of alcohol per mole of aluminum. See, for example, Rinse U.S. Pat. No. 3,054,816. Apparently, it is possible to reverse the order of addition so that the cyclic aluminum isopropoxide trimer is added after the acids are introduced into the petroleum oil; see, for example, column 4 of Bailey et al U.S. Pat. No. 3,776,846. The alcohol thus produced as a by-product is removed by distillation.

So far as is now known, no one has heretofore commercially employed oxyaluminum acylates in combination with organic acids to prepare greases of mineral oils in such a way as to avoid the problem of removing alcohol produced as a by-product in the grease manufacture and to avoid the addition and/or removal of water present in a system. In Rinse U.S. Pat. No. 3,054,816 (see column 3, lines 53–57), it is suggested that a cyclic aluminum oxide stearate trimer can be mixed with mineral oil and then reacted with benzoic acid at elevated temperature to produce a grease. This suggestion of Rinse, so far as is known, has never been commercially exploited. Moreover, the properties of the grease made by the Rinse procedure are not equivalent to the properties of greases made by using oxy aluminum acylates wherein the rate of the number of aromatic radicals to aliphatic radicals of the cyclic timer compound range from about 2:3 to 3:1.

In Harson British Pat. No. 825,878 cyclic organoaluminum timers and linear organoaluminum polymers are used in greases. Thus, mixed benzoate/stearate oxyaluminum acylate trimers are shown (see page 4, lines 100–110, Example 3, and Example 17 of Harson), as are greases made with cyclic trimers (see Examples 25 and 28. Harson used only low amounts of benzoic acids in his organoaluminum compounds (not more than 35 mole %) and he experienced difficulty in making smooth greases without lumping. In Example 28 thereof for example, when benzoic acid is present in the "external acids," certain other acids (such as branched chain and short chain acids or dimer acids or unsaturated acids or hydrogenated castor fatty acids must be present. Also, presolution of benzoic acid is needed to get a smooth grease. Harson never utilized oxyaluminum acylates wherein the ratio of number of aromatic radicals to aliphatic radicals of the cyclic timer compounds ranged from about 2:3 to 3:1.

BRIEF SUMMARY OF THE INVENTION

In one aspect, the present invention is directed to a class of new and very useful mixed aromatic/aliphatic oxyaluminum acylates. These acylates may be represented either by the formula:

or by the formula:

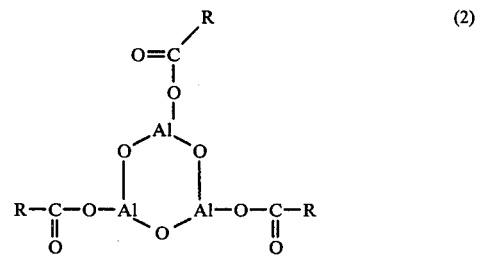

wherein R is selected from the group of radicals consisting of type (A) radicals and type (B) radicals where:

type (A) radicals consist essentially of aliphatic radicals each containing from 15 to 38 carbon atoms, and type (B) radicals consist essentially of aromatic radicals each containing from 6 to 16 carbon atoms.

Also, in any given group of such formula (1) and/or formula (2) compounds, the ratio of the number of radicals of said type (B) radicals to said type (A) radicals ranges from 2:3 to 3:1

In another aspect, the present invention relates to a process for making compounds of formulas (1) and (2) using lower alkanoic acids.

In another aspect, the present invention relates to premix compositions for use in grease manufacture which compositions comprise on a 100 weight percent total weight basis:

(A) from about 30 to 70 weight percent of at least one group of compounds of this invention as defined above, and, correspondingly (B) from about 70 to 30 weight percent of a petroleum derived hydrocarbon liquid having a viscosity at 100° F. ranging from about 35 to 50,000 SUS or of any other suitable liquid which would be compatible with grease systems such as a synthetic oil or ester of the type conventionally used or known to be compatible with synthetic lubricating oil systems.

In such a composition, the above indicated component (A) is uniformly dispersed in the above indicated component (B). As used herein, the term "dispersed", "dispersion", or the like is inclusive of both solutions and suspensions. Preferably, such a composition of this invention has the component (A) substantially completely dissolved in the component (B). This aspect further provides methods for the preparation of such compositions. It is noted that the terms "component (A)" and "component (B)" used herein are different from the terms "type (A) radicals" and "type (B) radicals" and should not be confused with each other.

In another aspect, this invention relates to an improved process for making a grease. This process involves the step of converting compounds of this invention as above defined in formulas (1) and/or (2) which are dispersed (preferably dissolved) in an oil (preferably a petroleum derived hydrocarbon oil) by reaction with a carboxylic acid material into a hydroxyaluminum diacyl soap directly without the production of by-product alcohol and without water being present. The following chemical equations are illustrative of this addition reaction whereby no by-products are formed:

Equation I where the compounds of this invention are represented by formula (1)

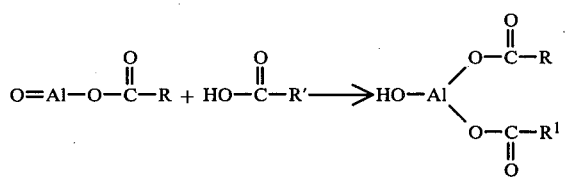

Equation II where the compounds of this invention are represented by formula (2)

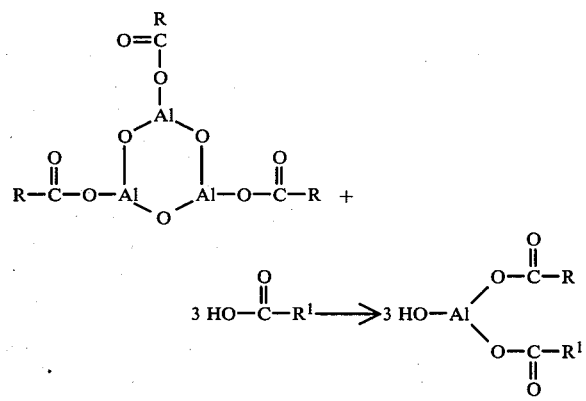

Where R is a mixture of aliphatic and aromatic radicals and R' is either aromatic, aliphatic or mixtures thereof, said R' radicals being supplied by the acids added by grease manufacturers practicing this process. For example, by one presently preferred procedure of this invention, this process involves the steps of heating a mixture of a group of compounds of this invention as above defined in formulas (1) and (2) with a petroleum derived hydrocarbon having a viscosity at 100° F. ranging from about 35 to 50,000 SUS (though higher and lower viscosity oils may be used if desired) until substantially all of the compounds of this invention are substantially completely dissolved in such petroleum oil. Thereafter, to such resulting solution is added at least one carboxylic material selected from the group consisting of aliphatic carboxylic acids, aromatic carboxylic acids and mixtures thereof, as more particularly hereinbelow defined. Thereafter, the temperature of the resulting system is raised and maintained at some elevated temperature until at least some of the compounds of this invention present in the system are converted to hydroxyaluminum diacylate soap through reaction with the acids added thereto. In another aspect of this invention, the carboxylic acids can be added to the lubricating oil base first and then the compounds of this invention added to the resulting system.

Finally, in another aspect, this invention relates to improved greases produced by such grease making process of the present invention. In making such an improved grease, the carboxylic acids can be added to the starting oil base first and then the compound(s) of this invention added to this resulting system, or otherwise, if desired.

A principal feature of the present invention is the creation of smooth, clear greases in a simple and reliable manner. No special pains are needed to predissolve the benzoic acid (e.g. aromatic acid) used with the compounds of this invention as above defined in formulas (1) and (2) and no special sequential addition and treating is needed. Both the aromatic acid (e.g. benzoic acid) and the aliphatic acid (e.g. fatty external acids) can be added simultaneously as a solid powder mixture, if desired, and a smooth, clear grease is characteristically obtained.

Another principal feature of the present invention is that such mixed aromatic oxyaluminum acylates (as defined hereinabove permit one to prepare a grease having excellent and controllable high viscosity characteristics compared to the prior art (see, for example, Rinse U.S. Pat. No. 3,054,816).

Another feature of the present invention is that such aluminum acylates (as defined hereinabove) permit one to prepare a grease without the use of added water and without the production of any by-product alcohol whatsoever. The freedom from by-product alcohol formation is highly desirable both from an environmental standpoint and also from a process operational standpoint.

The grease products of this invention characteristically incorporate an aluminum complex soap which, as those skilled in the art appreciate, has reference to a mixture of aluminum soap molecules containing at least one hydroxyl anion for each aluminum cation and substantially two carboxylic acid anions per aluminum atom. By this invention, such an aluminum complex soap has two dissimilar acid anions, such as one aromatic (e.g. benzoate anion) and one saturated aliphatic (e.g. arachidate, stearate, or like fatty carboxylic acid anion). Such an aluminum complex soap is produced by chemical reaction with the mixed oxyaluminum acylates of this invention when the same are used to make a grease in accordance with teachings of the present invention. Specifically such an aluminum complex soap is generated in situ in a mineral oil continuous phase during the practice of the grease making process of this invention through reaction with carboxylic acid material, but unlike the in situ process of U.S. Pat. No. 3,345,291, no by-product alcohol is produced.

Characteristically, a controllable and uniform thickening of a starting petroleum composition is achieved by the practice of the process of the present invention using the mixed oxyaluminum acylates of this invention.

Other further objects, aims, purposes, features, advantages, uses and the like will be apparent to those skilled in the art from the present disclosure.

DETAILED DESCRIPTION

As those skilled in the art will appreciate, oxyaluminum acylates of which the mixed oxyaluminum acylates of this invention, as defined above in formulas (1) and (2) are examples, are believed presently to exist either in a monomeric form or in a cyclic trimeric form. The conditions under which one form exits as opposed to the other form are at this time completely unknown.

One class of preferred compounds of this invention are those wherein the type (A) radicals are derived from benzoic acid. Another class of preferred compounds of this invention are those wherein the type (A) radicals are derived from stearic acid or isostearic acid and wherein the type (B) radicals are derived from benzoic acid.

One class of preferred fish oils for use in this invention contains at least about 50 percent by weight of hydrogenated fatty acids of arachidic and behenic acids, such as "Hydrofol 2022-55," available from the Ashland Chemical Company of Columbus, Ohio, USA.

Any convenient method of making the mixed oxyaluminum acylates of formulas (1) and/or (2) may be employed.

In general the preparation procedure involves the reactions represented by the following equations:

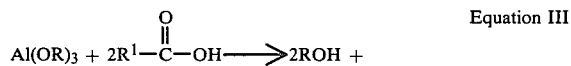

Equation III

Equation IV

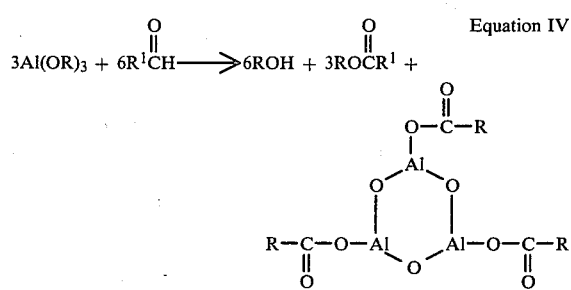

In the above equations R, is, for example, an isopropoxide radical (see Example 1 below). Equation III shows the reaction of preparing compounds represented by formula (1) and equation IV shows the reaction of preparing compounds represented by formula (2).

The desired number ratio of aliphatic radicals to aromatic radicals is achieved by controlling the composition of $R^1COOH$ in equation 3 and/or 4.

One presently preferred method of preparation involves a two step procedure. Thus, in a first step, two moles of carboxylic acid are combined with one mole of an aluminum trialkoxide (e.g. from about 82° to 150° C.) and reacted at an elevated temperature to form an aluminum alkoxy diacylate and two moles of an alcohol by-product (which is continuously distilled off) as illustrated by the following equation:

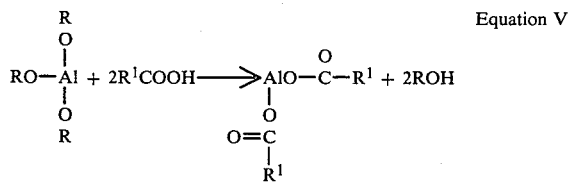

Equation V

Then, in second step, the product aluminum alkoxy diacylate is thermally decomposed conveniently at atmospheric pressures using, for example, a temperature of from about 150° to 250° C. The thermal decomposition results in a splitting off of an ester composed of the remaining (—OR) group and one of the acylate groups, as illustrated by the following equation wherein compounds of formula (1) are formed:

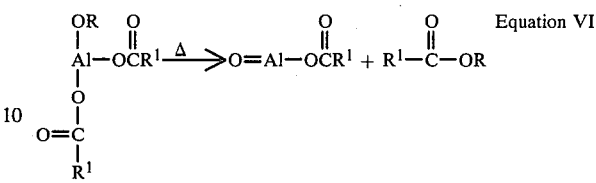

Equation VI

When making a long chain oxyaluminum acylate, where $R^1$ is derived from stearic acid, for example, the by-product ester is a high boiling acid and has to be removed by vacuum distillation. In a preferred procedure, however, the intermediate aluminum monoalkoxide diacylate is a mixed diacylate, where one of the acyl groups is a low molecular weight alkanoic acid. The ester is then formed with the acyl group of the lower molecular weight acid as the by-product, and this ester can be distilled off easily at atmospheric pressures. Thus, the higher molecular weight fatty acylate group is left behind to form the oxyaluminum acylate. Although Rinse in his U.S. Pat. No. 2,948,743 of Aug. 9, 1960 shows using acetic acid with stearic acid, this patent does not teach or suggest the preparation of the mixed oxy aluminum acylates of this invention. Acetic acid is a presently preferred lower alkanoic acid herein because of the characteristically low boiling points associated with acetate esters (isopropyl acetate, for example, boils at 88.4° C.).

The term "lower" as used herein has reference to a molecule or radical, as the reference may be, containing less than five carbon atoms per molecule.

The process of the present invention comprises the use of at least three acids, one of which is aromatic, and all three acids are add mixed together and reacted simultaneously with the aluminum tri-alkoxide. The amount of lower alkanoic (i.e. acetic) acid in such mixture is equal to one mole per mole of aluminum, and the other acids in the mixture together are equivalent to one mole mixed acids per mole of aluminum i.e., the acid mixtures can be:

|  |  |  |
|---|---|---|
| (a) | acetic acid | 1.0 mole |
| MIXTURE (1) | benzoic acid | 0.5 mole |
|  | stearic acid | 0.5 mole |
|  | or |  |
| (b) | acetic acid | 1.0 mole |
| MIXTURE (2) | benzoic acid | 0.4 mole |
|  | stearic acid | 0.6 mole |
|  | or |  |
| (c) | acetic acid | 1.0 mole |
| MIXTURE (3) | benzoic acid | 0.75 mole |
|  | stearic acid | 0.25 mole |

The above acid mixtures will produce oxyaluminum acylate compounds of formula (1) and/or formula (2) wherein R consists of a mixture of benzoyl and stearyl radicals in the following ratios: Acid mixture (1) will produce an R wherein the benzoyl to stearyl ratio is approximately 1:1, acid mixture (2) will produce an R wherein the benzoyl to stearyl ratio is approximately 2:3, and acid mixture (3) will produce an R wherein the benzoyl to stearyl ratio is approximately 3:1.

In compounds of this invention made by methods where a lower alkanoic acid such as acetic acid is used to produce a volatile ester byproduct, it is theorized (although not herein bound by theory) that minute amounts (1% or less) of the oxyaluminum lower alkanoate (such as oxyaluminum acetate) could be present. However, based on present available knowledge, these small quantities of such oxyaluminum lower alkanoate do not appear to adversely affect the properties of greases made from the aforesaid compounds of this invention.

Higher quantities of oxyaluminum lower alkanoate than those described in the previous paragraph can produce grease with interesting properties. Therefore, in another aspect of this invention, the amount of lower alkanoic acid can be increased and the amount of the mixture of higher alkanoic acid and aromatic acid can be correspondingly decreased (always maintaining approximately 2 moles of total acid, per atom of aluminum) so that when one mole of ester is produced per atom of aluminum by reaction thereof, an oxyaluminum acylate is also produced therewith which is represented by the formula (1) and/or formula (2) wherein R consists of a mixture of three types of radicals, i.e., type (A) radicals consisting from 15 to 38 carbon atoms, type (B) radicals consisting essentially of aromatic radicals containing from 6 to 16 carbon atoms and type (C) radicals consisting essentially of aliphatic radicals containing less than 5 carbon atoms per molecule. By way of illustration using stearic acid (to produce the type (A) radicals) benzoic acid (to produce the type (B) radicals) and acetic acid (to produce the type (C) radicals) the following starting acid materials are shown:

| Starting Acid Mixture (4) | |
| --- | --- |
| acetic acid | 1.5 mole |
| benzoic acid | 0.25 mole |
| stearic acid | 0.25 mole |
| Starting Acid Mixture (5) | |
| acetic acid | 1.1 moles |
| benzoic acid | 0.45 moles |
| stearic acid | 0.45 moles |

Starting mixtures (4) and (5) will produce oxyaluminum acylates represented by the formula (1) and or (2) wherein R would consist of a mixture of stearyl, benzoyl and acetyl radicals in the following ratios: starting mixture (4) will produce an R with a stearyl:benzoyl:acetyl ratio of 0.5:0.5:1 and acid mixture (5) will produce an R with a stearyl:benzoyl:acetyl ratio of 4.5:4.5:1.

The reaction sequence used to make a compound of this invention (see equation III and/or equation IV) can be carried out in organic liquid phase or in some cases it can be carried out as a mass reaction ("neat"). Particularly when it is desired to use the product mixed oxyaluminum acylate in grease making (as herein described and illustrated), it is preferred, but not necessary, to conduct the synthesis in a mineral oil or ester of the type which approximates that which it is anticipated will be used subsequently for an actual grease making operation. Then, the product as synthesized can be used directly for grease making without further preparative procedures.

However, when, for example, it is desired to make such a mixed oxyaluminum acylate of formula (1) and/or (2) in a purified or concentrated form, then the synthesis reaction(s) can be conducted in some cases without solvent or in a relatively low boiling organic inert (as respects reaction products) solvent. Afterwards (if conducted in a solvent) this solvent can be removed by vacuum distillation preferably at reduced pressures to leave a purified, concentrated product. When, for example, such a concentrated product comprised of a compound of this invention is to be used for viscosity regulation of a liquid curable polyester resin system in a vinyl monomer, such as styrene, such concentrated product can be dissolved in such styrene and the resulting solution then added to the polyester resin in a desired amount.

A presently preferred composition for use in grease manufacture comprises on a 100 weight percent total weight basis:
(A) from about 30 to 70 weight percent of at least one group of compounds of formula (1) and/or formula (2) and, correspondingly,
(B) from about 70 to 30 weight percent of a petroleum derived hydrocarbon having a viscosity at 100° F. ranging from about 35 to 50,000 SUS, said component (A) being uniformly dispersed in said component (B).

In preferred grease making compositions, component (A) is dissolved in said component (B).

Any conventional method may be employed to make an intermediate grease making composition of this invention. One presently preferred method involves, as a first step, admixing at least one aluminum trialkoxide with a mineral oil which has a viscosity at 100° F. of from about 35 to 50,000 SUS and which has dispersed therein from about 30 to 72 weight percent of a carboxylic acid mixture based upon the total comined weight of such compounds and said mineral oil. Aluminum trisopropoxide is presently preferred because of its availability and the relatively low boiling point of its alcohol and esters; however, other alkoxides may be used such as aluminum tri sec butoxide, and the like. The total amount of such aluminum tri alkoxide so admixed is equal to about one mole aluminum alkoxide per two moles of acid. At least one lower alkanoic acid (preferably acetic) is also present as part of the acid mixture in the system.

Next, one heats the resulting system to a temperature where alcohol derived from such lower alkoxide groups begins to distill off.

Heating is continued until two moles of the alcohol are distilled off on a theoretical basis.

Then, one further heats such system to a temperature where a lower alkyl lower alkanoate ester derived from such remaining lower alkoxide group and such lower carboxylate radical begins to distill off therefrom, and one maintains such system at such temperature until about one mole of such ester has been so distilled off, on a theoretical basis.

In the carboxylic acid mixture, the molar ratio of aromatic to aliphatic (higher alkanoate) radicals, ranges from about 2:3 to 3:1, each aliphatic (higher) molecule of which contains from about 15 to 38 carbon atoms, and, correspondingly, each aromatic carboxylic acid molecule of which contains from about 6 to 16 carbon atoms. The quantity of lower alkanoic acid present initially ranges from about 0.9 to 1.1 mole per mole of aluminum trialkoxide.

To make a grease of this invention using a mixed oxyaluminum acylate of formula (1) and/or (2), for example, one employs a mineral starting oil having a viscosity at 100° F. of from about 35 to 50,000 SUS. In such oil, at least one carboxylic acid material is contacted with such mixed oxyaluminm acylate with preferably both reactant types being dispersed (more preferably dissolved) in the oil. Such contacting carried out at a temperature sufficient to produce reaction between said carboxylic acid material and said oxyaluminum acylated compound, and such contacting is continued until at least some of such oxyaluminum acylate compound has been converted into an aluminum soap. The product aluminum soap is an hydroxy aluminum diacylate. The resulting grease containing such hydroxy aluminum diacylate is then milled and packaged. It can be milled at room temperatures or at any elevated temperatures up to about 200° C. with temperatures below about 150° C. being presently preferred.

In one presently preferred grease making grease process of the present invention, the following steps are employed:

First, one heats mixture of petroleum derived hydrocarbon oil having a viscosity at 100° F. of form about 35 to 50,000 SUS and a grease making composition as above described. This mixture contains a total amount of aluminum in the range from about 0.01 to 2.0 weight percent based on total mixture weight. Such heating is conducted at temperatures, and for times, sufficient to substantially completely dissolve all starting mixed oxy aluminum acylates present in said hydrocarbon oil.

Next, one admixes with the resultant such mixture of step (A) a total of from about 0.8 to 1.2 moles (based on the total quantity of aluminum present in said resultant such mixture) of at least one carboxylic acid material selected from the group consisting of aliphatic monocarboxylic acids containing from 15 through 40 carbon atoms each and aromatic monocarboxylic acids containing from 6 through 16 carbon atoms each, Finally, one heats and gradually raises the temperatures of the product mixture, all the while agitating such product mixture, until at least some of such staring mixed oxyaluminum acylates present in the first step have been converted into hydroxy aluminum diacylates aluminum soap by reaction in situ with said carboxylic acid material.

As indicated, in such grease making process of this invention, the starting mixed oxyaluminum acylates of formula (1) and/or formula (2) present in a base oil are reacted at least partially (preferably substantially completely) with carboxylic acid materials. A starting such mixed oxyaluminum acylate provides from a stoichiometric standpoint approximately one-half of the acylate radicals needed to produce an aluminum soap which is formed from the reaction of such mixed oxyaluminum acylate with carboxylic acid material, such aluminum soap being a compound which contain approximately two acyl groups and one hydroxyl group each group being directly bonded to an aluminum atom (one name for such soap being hydroxy aluminum diacylate).

In calculating the molar quantity of carboxylic acid material to be used (added) for reaction with a mixed oxyaluminum acylate in making a grease according to this invention (based on the number of carboxyl groups present in the carboxyl acid material) it is sometimes convenient to use a mole ratio ranging from about 0.8 to 1.2 of total quantity of carboxylic acid material to total quantity of mixed oxyaluminum acylate.

In a grease prepared by the teachings of this invention, such an aluminum soap is preferably characterized by having the total number of acyl radicals of any given soap molecule composed of a weight ratio of aliphatic acyl groups to aromatic acyl groups ranging from about 1.3:0.7 to 0.7:1.3. Presently preferred aliphatic acyl groups are derived from fatty carboxylic acids each having an aliphatic group of at least about 16 carbon atoms. Also, presently preferred aromatic acyl groups are derived from benzoic acid.

In a grease prepared by the teachings of this invention, it is not necessary to have all of the starting mixed oxyaluminum acylate compounds converted to such an aluminum soap, although for reasons of obtaining a maximum thickening of a given base oil based upon a given quantity of mixed oxyaluminum acylate in admixture therewith, it is presently preferred to achieve a substantially complete conversion of staring mixed only aluminum acylate compounds into aluminum soap. However, partial conversion is sometimes preferred as when, in a given grease manufacturing situation, excess mixed oxyaluminum acylate beyond a theoretical or calculated quantity of mixed oxyaluminum acylate is added to a starting reaction system so as to permit processing flexibility. For example, with such an excess quantity, in solution in an oil, one can add only sufficient carboxylic acid material as is necessary to achieve some predetermined system viscosity at some predetermined processing temperature, such a system viscosity having previously been determined to be characteristic of a given grease viscosity desired at ambient temperatures, according to the wishes of a given grease maker in some given instance. Such a grease could be further thickened by adding more acid later, or such a grease could be used as a "master batch" (that is, more oil and acid could subsequently be added thereto).

Although in making a grease in accordance with this invention, it is presently preferred to use, as the starting organo aluminum compound which is convertible into aluminum soap by reaction with carboxylic acid materials, only a mixed oxy aluminum acylate as defined above in formulas (1) and/or (2) (because of the circumstance that no by-product alcohol is produced in converting this compound to an aluminum soap), nevertheless, as those skilled in the art will appreciate, such mixed oxyaluminum acylates may be used, if desired, in combination with other such staring organoaluminum compounds known to the prior art of grease making by forming aluminum soaps. For example, a grease maker may desire to use up stocks on hand of such prior art organaluminum compounds gradually, or he may desire to use the compounds of this invention in combination with such prior art materials as aluminum stearate for reasons of economy or for other reasons.

In general, when such a starting organoaluminum compound mixture is used, it is preferred to employ a mixture wherein at least about 50 weight percent thereof, on a total mixture weight basis, is comprised of mixed oxyaluminum acylate as defined above in formulas (1) and/or (2).

In its reaction with mixed oxy aluminum acylates, the hydroxyl group of a carboxyl moiety automatically goes to the aluminum of the starting mixed oxy aluminum acylate as the soap is being formed.

In addition or in admixture with to petroleum derived (mineral) grease making base oils, suitable specialized starting oils adapted for use in the grease making process of the present invention include lubricating oils of naphthenic base, paraffinic base hydrocarbons, mixed base mineral oils, vegetable oils, synthetic oils, including synthesized hydrocarbon base fluids, alkylene polymers, polysiloxanes, ester-type oils such as dicarboxylic acid ester type oils, liquid esters of phosphorous acids, such as are shown in U.S. Pat. No. 2,768,138), and the like. In general, preferred starting base oils have viscosities at 100° F. ranging from about 35 to 50,000 SUS.

To make a grease using compounds of formulas (1) and/or (2) in an oil, a grease maker need use no particular type of carboxylic acid material for reaction therewith. For example, it now appears that the teachings of the prior art with respect to the use of various carboxylic acids, combinations thereof, order of contacting, temperature conditions, and the like in connection with the use of the prior art aluminum alkoxides in grease making can be employed to make greases from compounds of formula (1) and/or (2), except that here no by-product alcohol is produced and no water is needed. Mono and dicarboxylic acids can be used, as can halo substituted such acids like chloroacetic acid dichloroacetic acid, and the like. Examples of suitable dicarboxylic acids include succinic. One particularly preferred monocarboxylic acid is presently isostearic because such acid which is a branched $C_{18}$ saturated acid, is a relatively low viscosity liquid at ambient conditions and tends to bring down the melting point and softening point of derivatives thereof, including especially aluminum soaps thereof. For examples of U.S. patents teachings extremely wide variability in types of acids that can be added to an oil for reaction with the mixed oxyaluminum acylates of this invention to make an aluminum soap, as desired in grease making, see U.S. Pat. No. 3,476,684 (involving mono and dichloro acetic acids), U.S. Pat. No. 3,413,222 (involving succinic acid). Dimer acids, such as dimerized vegetable oil carboxylic acids, such as are offered commercially by Emery Industries, can also be used as the carboxylic acid material.

A presently preferred class of compounds within the scope of formulas (1) and/or (2) comprises such compounds wherein the number ratio of such Type (B) radicals to such Type (A) radicals ranges from about 2:3 to 3:1. In such class, the Type (B) radicals are preferably derived from benzoic acid. Such preferred compounds are relatively easy for a grease maker to convert into a grease in the presence, for example, a hydrocarbon oil. Such compounds containing a higher ratio of benzoic acids to aliphatic acids than is disclosed in the prior art, presently appear to be particularly desirable in grease making because a smaller quantity of benzoic acid is subsequently needed to complete the in situ reaction which forms the hydroxy aluminum stearate/benzoate soap. Benzoic acid itself is difficult for a grease maker to handle because of its tendency to sublime at temperatures above 100° C. Another advantage is the circumstance that, when using such a high benzoic acid derivative, one does not have to be concerned about the exact order of sequential addition of the carboxylic acid materials being reacted therewith in grease making. Both aromatic and aliphatic acids can be added simultaneously to the synthesis reaction zone. With mixed oxyaluminum acylates of the prior art which are relatively low in benzoic acid content (that is, whose content of such acid is lower than the bottom of the radical ratio just above indicated), one apparently should follow a sequential acid addition procedure (involving, for example, the addition first of long chain aliphatic fatty acid before adding benzoic acid) in order to produce a maximum thickening of oil base for a minimum total quantity of such mixed oxyaluminum ayclate. Also, with such a high benzoic acid derivative, it may be that it is not necessary to have a complete reaction with mixed oxy aluminum acylate compound to produce such a maximum viscosity increase for a minimum amount of such mixed oxyaluminum acylate compound of this invention, there is presently at hand no conclusive data on this point. Further, it may be that the effect of sequential addition of carboxylic acid material is not as pronounced in this invention as it apparently is with the prior art aluminum alkoxides (see, for example, Polishuk U.S. Pat. No. 3,591,505), but, as indicated above, in the present invention, no by-product alcohol is formed during grease manufacture.

Greases made with mixed oxyaluminum acylates as provided by the teachings of this invention can be formulated with the various additives heretofore employed in the grease making art, if desired. Thus, for example, a grease of this invention can contain one or more of such additives as rust inhibitors, anti-corrosion agents, antioxidants, dispersants, fillers, metal deactivators, pressure or antiwear agents, tackiness agents or systems, and the like, as those skilled in the art will appreciate. Such additives may be added to a grease prior to, during, or after the aluminum soap forming step following the teachings of this invention. The quantity of additives in any given grease can, of course, vary, but a presently preferred preference is to employ less than about 15 weight percent (total grease weight basis) of such additives so as to aim toward quality product greases.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specifications.

EXAMPLE 1

Preparation of Mixed Oxyaluminum Acylate

To a three neck 500 ml flask or pot is added 100 grams of a grease base oil having a vixcosity at 100° F. of 1766 SUS. This is a dark, amber, heavy viscous oil mixture used for grease manufacture. To this oil in such flask is added 30 grams of acetic acid, 71 grams of hydrogenated tallow fatty acids and 30.5 grams of benzoic acid and finally 102.1 grams aluminum isopropoxide. This mixture is stirred and the temperature gradually increased to a point where isopropanol begins to distill off. As the distillation continues, temperature readings are taken at 30 minute intervals and the following Table results:

TABLE 1

| POT TEMPERATURE | VAPOR TEMPERATURE |
|---|---|
| 95° C. | 82° C. |
| 88° C. | 82° C. |
| 88° C. | 82° C. |
| 93° C. | 82° C. |
| 110° C. | 82° C. |
| 120° C. | 82° C. |
| 172° C. | 83° C. |
| 190° C. | 89° C. |
| 210° C. | 90° C. |
| 215° C. | 80° C. |
| 230° C. | 88° C. |

During the distillation, a total of 2 moles of isopropyl alcohol are removed after which one mole of isopropyl acetate is removed, all on the theoretical basis. The reaction mixture is thereafter allowed to cool to room temperature. The product assays at 5.72 percent aluminum, indicating a 51.9 percent solution of mixed oxyaluminum stearate/benzoate with a stearate/benzoate mole ratio of 1:1 in grease base oil. At room temperature, this product is a soft paste having a generally clear dark amber hue. This product is pourable at a temperature of about 50°–60° C.

In place of the grease base oil, one may employ any inert solvent medium having a relatively high boiling point, such as, for example, Magie Oil No. 47 (which is an all aliphatic oil made by Magie Oil Company having an approximate boiling point of 240° C.), an ester, such as one of the type used to make synthetic lubricating oils, or the like.

EXAMPLE 2

Grease Preparation

To 85 grams of the same grease base oil as employed in Example 1 contained in a beaker is added 10.2 grams of the product obtained in Example 1. The resulting mixture is stirred and gradually heated to 110° C. where it is observed that a clear solution results. At this point, there is added to the heated system simultaneously 3.7 grams of hydrogenated tallow fatty acid and 1.1 gram of benzoic acid with stirring. The amount of the acids added in this grease making example is calculated in such a manner as to produce a "final soap" in situ which has a molar ratio of 1.1 to 0.9 fatty to benzoyl groups and which contains one hydroxyl group per aluminum atom. Heating is continued and the temperature is gradually raised to 140° C. After the acids are added a slight haze forms which disappears by the time the temperature reaches 140° C. With continued heating, the temperature of the system is thereafter gradually increased to 180° C. at which time heating is discontinued. After the acids are added, and as the temperature is thus gradually increased, gradual thickening of the system is observed. The thickening takes place in less than one hour due to the elimination of the step where alcohol is boiled off.

The product at room temperature is a clear grease, dark amber in color.

The thickening during heating as above described indicates the occurrence of a reaction between the oxyaluminum stearate benzoate and the added acids. It is believed thickening does not occur unless hydroxyl groups are present. Therefore, the reaction involved is representable by the following illustrative equation:

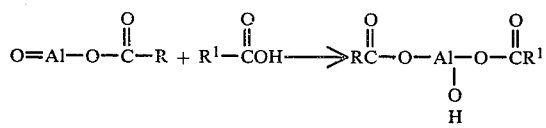

Where R represents a mixture of fatty acid radicals and benzoic acid radicals in a molar ratio of 1:1 present in the oxyaluminum acylate starting material and R' represents a mixture of fatty acid radicals and benzoate acid radicals in a molar ratio of 1.2 to 0.8 added during grease manufacture. Thus, this grease product contains a diacyl mono hydroxy aluminum soap derived from the starting oxyaluminum stearate benzoate, from Example 1, through reaction with the added stearic and benzoic acids. Said soap containing a molar ratio of 1.1 to 0.9 fatty radicals to benzoyl radicals and having approximately one hydroxyl group per aluminum atom.

In this Example, the stearic acid could have been added before the benzoic acid, if desired. Also in this example, the ratio of acids added could be changed so that the final soap contains a molar ratio of 1:1 fatty radicals to benzoyl radicals or any other ratio desired.

In this Example, the starting materials are substantially anhydrous. No water or alcohol is added to the system during processing and no water or alcohol is evolved from the system during processing. Further, no water or alcohol is found to be present in the system after processing.

EXAMPLE 3

To a 500 ml three neck flask is added 76.9 g of a naphthenic base lubricating oil having a viscosity of 172 SUS (Saybolt Universal Seconds) at 100° F. To this oil is added 36.4 g hydrogenated tallow fatty acids, 31.3 grams benzoic acid, 23.1 g acetic acid, and finally 78.5 grams aluminum isopropoxide. This mixture is stirred and the temperature gradually increased to a point where isopropyl alcohol begins to distill off. As the distillation continues, temperature readings are taken at 60 minute intervals and the following table results:

TABLE II

| POT TEMPERATURE | VAPOR TEMPERATURE |
|---|---|
| 90° C. | 82° C. |
| 90° C. | 82° C. |
| 127° C. | 82° C. |
| 177° C. | 93° C. |
| 207° C. | 105° C. |
| 202° C. | 98° C. |
| 205° C. | 95° C. |

During the distillation, a total of 2 moles of isopropyl alcohol are removed after which one mole of isopropyl acetate is removed, all on the theoretical basis. The reaction mixture is thereafter allowed to cool to room temperature. The product is a high melting resiliant solid, dark amber and relatively clear. The aluminum was analyzed to be 6.19% which indicates a 50% solution of mixed oxyaluminum stearate (hydrdrogenated tallow) benzoate in 172 SUS naphthenic base oil. The product has a stearate to benzoate mole ratio of 1:2.

EXAMPLE 4

To 85 grams of the same grease base oil as employed in Examples 1 and 2 contained in a beaker is added 9.4 grams of the product from Example 3. The mixture is stirred and the temperature is raised to 170° C. and held for 45 minutes until the mixed aluminum acylate dissolved. The temperature is then allowed to recede to 110° C. at which point there is added to the system simultaneously 4.7 grams of hydrogenated tallow fatty acids and 0.8 grams benzoic acid with stirring. The temperature is then raised slowly to 180° C. at which time the heating is discontinued. Gradual thickening is observed after the acids are added and as the temperature is gradually increased. The product is a clear heavy grease, dark amber in color. The aluminum soap which was made in situ is a mixed soap with a molar ratio of 1.1 to 0.9, fatty to benzoyl radicals and which contains one hydroxyl group per aluminum atom.

EXAMPLE 5

To a 500 ml three necked flask is added 108.8 grams Magiesol 47 (Magie Bros. Oil Co., Franklin Park, Ill.)

which is an aliphatic solvent having a boiling point of approximately 470° F. To this solvent is added 75.73 grams hydrogenated tallow fatty acids, 16.28 grams benzoic acids and 81.68 grams aluminum isopropoxide. This mixture is under agitation and the temperatures slowly increased to a point where isopropyl alcohol starts to distill off. When the pot temperature reaches 115° C. and one mole of alcohol has been taken off on a theoretical basis, 24 grams of acetic acid are introduced into the reaction mixture through a dropping funnel. Agitation is continued and the flask temperature held between 115° and 122° C. until the second mole of isopropyl alcohol (theoretical basis) is distilled off. The temperature is gradually increased and isopropyl acetate begins to distill over. By the time the temperature reaches 246° C., one theoretical mole of isopropyl acetate has been distilled off. The reaction mixture is thereafter allowed to cool to room temperature. The product is a liquid light amber in color and substantially clear. The product was analyzed to contain 4.72% aluminum which indicates that the product is 47.5% oxyaluminum stearate/benzoate in agiesol 47 aliphatic solvent. The product has a stearate to benzoate mole ratio of 2:1 and is representative of the prior art compounds disclosed in Harson British Pat. No. 825,878.

EXAMPLE 6

283.5 grams of the same base oil as employed in Examples 1, 2, and 4, contained in a beaker is added 12.4 grams of the product from Example 5. The mixture is heated with stirring to a temperature of 130° C. at which temperature there is added to the system simultaneously 2.65 grams of hydrogenated tallow fatty acid and 1.5 grams of benzoic acid with stirring. As both acids are simultaneously added, it is observed that the resultant mixture of lubricating base oil, aluminum derivative and acids turns cloudy. The temperature is then raised to 200° C. for 15 minutes. During the time of increasing the temperature the cloud diminishes somewhat, but does not entirely disappear. Holding the mixture at a temperature of 200° C. for 15 minutes does not improve the clarity of the mixture. Although thickening occurs during the increasing of the temperature, the viscosity of the mixture is not as high as greases made with compounds of the present invention.

EXAMPLE 7

To a 500 ml three neck flask is added 78.1 grams isopropyl octoate. To this high boiling ester is added 51.1 grams isostearic acid (Emersol 875, Emery Industries, Inc.), 21.9 grams benzoic acid, 21.6 grams acetic acid and finally 73.5 grams aluminum isopropoxide. This mixture is stirred and the temperature gradually increased to a point where isopropyl alcohol begins to distill off. As the distillation continues, temperature readings are taken at bi-hourly intervals and the following table results:

TABLE III

| POT TEMPERATURE °C. | VAPOR TEMPERATURE °C. |
| --- | --- |
| 97 | 82 |
| 125 | 85 |
| 156 | 88 |
| 176 | 105 |
| 180 | 100 |
| 180 | 98 |
| 185 | 93 |
| 194 | 98 |

TABLE III-continued

| POT TEMPERATURE °C. | VAPOR TEMPERATURE °C. |
| --- | --- |
| 201 | 104 |

During the distillation, a total of 2 moles of isopropyl alcohol are removed after which one mol of isopropyl acetate is removed, all on a theoretical basis. The reaction mixture is thereafter allowed to cool to room temperature. The product is a light amber liquid relatively clear. The aluminum was analyzed to be 5.70% which indicates a 50% solution of oxyaluminum isostearate/benzoate in isopropyl octoate. The product has an isostearate to benzoate mole ratio of 1:1, and can be converted to the solvent free state by distilling off the isopropyl octoate preferably under reduced pressure.

EXAMPLE 8

To 84.5 grams of the same grease base oil as employed in Example 1 contained in a beaker is added 10.8 grams of the product solution obtained in Example 7. The resulting clear mixture is stirred and gradually heated to 90° C. At this point, there is added to the heated system simultaneously 3.2 grams hydrogenated tallow fatty acids and 1.4 grams benzoic acid with stirring. The amount of the acids added in this example is calculated in such a manner as to produce a "final soap" in situ which has a molar ratio of 1:1 fatty to benzoyl groups and which contains one hydroxyl group per aluminum atom and can be described as a ballanced mixed soap. The temperature is then raised slowly to 190° C. at which time the heating is discontinued. Gradual thickening is observed after the acids are added and as the temperature is increased. The product is a clear, heavy grease, dark amber in color.

EXAMPLE 9

To 84.5 grams of the same grease base oil as employed in Example 1 contained in a beaker is added 10.4 grams of the product solution obtained in Example 7. The resulting clear mixture is stirred and gradually heated to 90° C. At this point, there is added to the heated system simultaneously 3.7 grams hydrogenated tallow fatty acids and 1.1 grams benzoic acid with stirring. The temperature is then raised slowly to 190° C. at which time the heating is discontinued. Gradual thickening is observed after the acids are added and as the temperature is increased. The product is a clear, heavy grease, dark amber in color. The aluminum soap which was made in situ in this example is a mixed soap with a slightly unbalanced molar ratio of fatty to benzoyl groups of 1.1 to 0.9 and contains one hydroxyl group per aluminum atom.

I claim:
1. Compounds of the formula

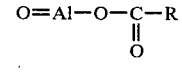

and of the formula

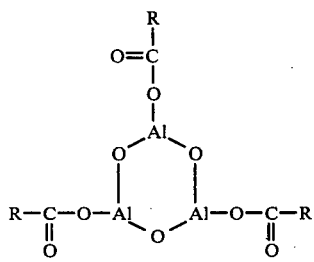

wherein R is selected from the group of radicals consisting of:
Type (A): aliphatic radicals each containing from 10 to 38 carbon atoms, and
Type (B): aromatic radicals each containing from 6 to 16 carbon atoms, and
wherein, in any given group of such compounds, or mixtures of such group, the ratio of the number of radicals of said type (B) to said type (A) ranges from 2:3 to 3:1.

2. Compounds of claim 1 wherein said type (A) radicals are derived from hydrogenated tallow acids and said type (B) radicals are derived from benzoic acid.

3. Compounds of claim 1 wherein type (A) radicals are derived from hydrogenated fish oil acids and said type (B) radicals are derived from benzoic acid.

4. Compounds of claim 1 wherein said type (A) radicals are derived from stearic acid and said type (B) radicals are derived from benzoic acid.

5. Compounds of claim 1 wherein said type (A) radicals are derived from isostearic acid and said type (B) radicals are derived from benzoic acid.

6. A composition for use in grease manufacture comprising on a 100 weight percent total weight basis
(A) from about 30 to 70 weight percent of at least one group of compounds of claim 1, and, correspondingly,
(B) from about 70 to 30 weight percent of a petroleum derived hydrocarbon having a viscosity at 100° F. ranging from about 35 to 50,000 SUS.
said component (A) being uniformly dispersed in said component (B).

7. The composition of claim 6 wherein said component (A) is dissolved in said component (B).

8. The composition of claim 6 wherein in said component (A), said type A radicals are comprised of stearyl and said type (B) radicals are comprised of benzyl.

9. The composition of claim 6 wherein said type (A) radicals are derived from hydrogenated tallow acids, and said type (B) radicals are derived from benzoic acid.

10. The composition of claim 6 wherein said type (A) radicals are derived from hydrogenated fish oil and said type (B) radicals are derived from benzoic acid.

11. The composition of claim 6 wherein said type (A) radicals are derived from isostearic acid and said type (B) radicals are derived from benzoic acid, and said type (b) radicals are derived from benzoic acid.

12. A process for making a grease comprising the steps of
(A) heating a mixture of petroleum derived hydrocarbon having a viscosity at 100° F. of from about 35 to 50,000 SUS and a composition of claim 6, said mixture containing a total amount of aluminum in the range from about 0.01 to 2.0 weight percent based on total mixture weight, said heating being conducted at temperatures, and for times, sufficient to substantially completely dissolve all starting mixed oxyaluminum acylates present in said hydrocarbon,
(B) admixing with the resultant such mixture of step (A) a total of from about 0.8 to 1.2 moles based on the total quantity of aluminum present in said resultant such mixture of at least one carboxylic acid material selected from the group consisting of aliphatic monocarboxylic acids containing from 10 through 40 carbon atoms each and aromatic monocarboxylic acids containing from 7 through 28 carbon atoms each, and
(C) thereafter heating and gradually raising the temperature of the product mixture until at least some of said starting mixed oxyaluminum acylates present in step (A) have been converted into diacyl monohydroxy aluminum soap by reaction in situ with said carboxylic acid material.

13. A grease prepared by the process of claim 12.

14. In an improved process for making a grease from a starting oil having a viscosity at 110° F. of from about 35 to 50,000 SUS by contacting in said oil at least one carboxylic acid material with starting organoaluminum compound, both said carboxylic acid material and said organoaluminum compound being dispersed in said oil, said contacting being carried out at a temperature sufficient to produce reaction between said carboxylic acid material and said organoaluminum compound, said contacting being continued until at least some of said organoaluminum compound has been converted into an aluminum soap and a grease is formed, the improvement with comprises employing as said starting organoaluminum compound at least one compound of claim 1, and wherein said aluminum soap is an aluminum monohydroxy diacylate.

15. The process of claim 14 wherein in said starting organoaluminum compound said type A radicals are derived from a member of the class consisting of hydrogenated tallow acids and hydrogenated fish oil acids and type B radicals derived from benzoic acid.

16. The process of claim 14 wherein the total amount of aluminum present is in the range from about 0.01 to 2.0 weight percent based on total weight of said starting oil and said organoaluminum compound.

17. The process of claim 14 wherein said starting organoaluminum compound is initially substantially completely dissolved in said oil before said carboxylic acid material is admixed with said oil.

18. The process of claim 14 wherein said carboxylic acid material is initially substantially completely dissolved in said oil before said starting organoaluminum compound is dispersed in said oil.

19. A grease prepared by the process of claim 14.

20. The process of claim 12 wherein step (A) is practiced before step (B).

21. The process of claim 12 wherein said carboxylic acid material so admixed comprises isostearic acid.

22. A grease prepared by the process of claim 23.

23. The compounds of claim 1 wherein said type (B) aromatic radicals are derived from benzoic acid.

24. A process for making a grease comprising the steps of:
(A) heating a mixture of (a) petroleum derived hydrocarbon having a viscosity at 100° F. of from about 35 to 50,000 SUS, (b) a composition of claim 6, and (c) at least one carboxylic acid material selected from the group consisting of aliphatic monocarboxylic acids containing from 10 through 40 carbon atoms each and aromatic monocarboxylic acids containing from 7 through 28 carbon atoms each, said mixture containing a total amount of aluminum in the range of from about 0.01 to 2.08% based on total mixture weight, said mixture further containing a total of from about 0.8 to 1.2 moles based on the total quantity of aluminum present in said mixture of said carboxylic acid material, said heating being conducted at temperatures, and for times, sufficient to substantially completely dissolve all starting mixed oxyaluminum acylates present in said hydrocarbon, and (B) thereafter heating and gradually raising the temperature of the product mixture until at least some of said starting mixed oxyaluminum acylates present in step (A) have been converted into diacyl monohydroxy aluminum soap by reaction in situ with said carboxylic acid material.

25. A process for making a grease comprising the steps of:
(A) heating a mixture of a petroleum derived hydrocarbon having a viscosity at 100° F. of from about 35 to 50,000 SUS with at least one carboxylic acid material selected from the group consisting of aliphatic moncarboxylic acids containing from 10 through 40 carbon atoms each and aromatic monocarboxylic acids containing from 7 through 28 carbon atoms each, and mixtures thereof,
(B) admixing with the resulting mixture a composition of claim 6 so as to produce a product mixture containing from about 0.8 to 1.2 moles of said carboxylic acid material based on the total quantity of aluminum present in such product mixture containing a total amount of aluminum in the range of from about 0.07 to 2.08% based on total product mixture weight,
(C) first heating such product mixture at temperature and for times sufficient to substantially completely dissolve all starting mixed oxyaluminum acylates present, and
(D) secondly heating the resulting such product mixture and gradually raising the temperature thereof until at least some of said starting mixed oxyaluminum acylates present have been converted into diacyl monohydroxyl aluminum soap by reaction in situ with said carboxylic acid material.

26. A process for making oxyaluminum acylates of the formula

and of the formula

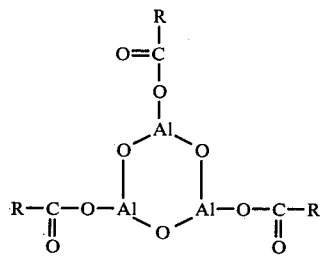

where R is selected from the group of radicals consisting of:
Type (A): aliphatic radicals each containing from 1 to 38 carbon atoms, and
Type (B): aromatic radicals each containing from 6 to 16 carbon atoms, and
wherein in any given group of such compounds or mixtures of such groups, the ratio of the number of radicals of said type (B) to said type (A) ranges from 2:3 to 3:1, said process comprising the steps of:
(A) admixing together
(1) an aluminum alkoxide of the formula $$Al(OR)_3$$

where R is a lower alkyl radical containing less than five carbon atoms,
(2) an acid mixture wherein each acid thereof has the formula $$R^1COOH$$

where $R^1$ is selected from the group consiting of
(a) aliphatic radicals each containing from 10 to 38 carbon atoms,
(b) aromatic radicals each containing from 6 to 16 carbon atoms, and
(c) lower alkyl radicals each containing less than four carbon atoms, the amount of such lower alkanoic acid in said acid mixture being equal to one mole per mole of aluminum in said aluminum alkoxide, and the respective amounts of said type (B) radicals to said type (A) radicals in any given said acid mixture ranging from 2:3 to 3:1,
(B) first heating the resulting mixture at a temperature of from about 82° to 150° C. for a time sufficient to form an aluminum alkoxy diacylate and two moles of an alcohol by-product which is continuously distilled off during said first heating,
(C) secondly heating the product of step (B) to a temperature of from about 150° to 250° C. to thermally decompose said aluminum alkoxy diacylate and produce said desired oxyaluminum acylate compounds and also produce an ester with said lower alkanoic acid which is continuously distilled off during said second heating.

* * * * *

UNITED STATES PATENT AND TRADEMARK OFFICE
CERTIFICATE OF CORRECTION

PATENT NO. : 4,280,917
DATED : July 28, 1981
INVENTOR(S) : Charles E. Pratt

It is certified that error appears in the above—identified patent and that said Letters Patent is hereby corrected as shown below:

Column 1, line 53, change "timer" to --trimer--.

Column 1, line 55, change "timers" to --trimers--.

Column 2, line 4, change "timer" to --trimer--.

Column 6, line 40, change "add mixed" to -- admixed --.

Column 8, line 32, change "comined" to --combined--.

Column 9, line 34, change the comma to a period: --.--.

Column 9, line 37, change "staring" to --starting--.

Column 10, line 13, change "staring" to --starting--.

Column 10, line 42, change "staring" to --starting--.

Column 11, line 66, change "ayclate" to --acylate--.

Column 12, line 42, change "vixcosity" to --viscosity--.

UNITED STATES PATENT AND TRADEMARK OFFICE
CERTIFICATE OF CORRECTION

PATENT NO. : 4,280,917

DATED : July 28, 1981

INVENTOR(S) : Charles E. Pratt

It is certified that error appears in the above—identified patent and that said Letters Patent is hereby corrected as shown below:

Column 14, line 40, change "resiliant" to --resilient--.

Column 14, line 43, change "hydrdrogenated" to --hydrogenated--.

Column 19, line 27 (claim 25), change "moncarboxylic" to --monocarboxylic--.

Column 20, line 33 (claim 26), change "consiting" to --consisting--.

Column 5, line 2, change "exits" to -- exists --.

Column 10, line 13, change "only" to -- oxy --.

Column 17, lines 57-58 (claim 11), place a period after "benzoic acid" and cancel ", and said type (b) radicals are derived from benzoic acid."

Column 18, line 32, (claim 14), change "with" to -- which --

Signed and Sealed this

Fourteenth Day of September 1982

[SEAL]

Attest:

GERALD J. MOSSINGHOFF

Attesting Officer    Commissioner of Patents and Trademarks